(12) United States Patent
Lenarz et al.

(10) Patent No.: US 10,213,597 B2
(45) Date of Patent: Feb. 26, 2019

(54) ELECTRODE LEAD THAT AVOIDS ELECTRODE ARRAY MIGRATION FROM THE COCHLEA

(71) Applicant: MED-EL Elektromedizinische Geraete GmbH, Innsbruck (AT)

(72) Inventors: Thomas Lenarz, Hannover (DE); Claude Jolly, Innsbruck (AT); Anandhan Dhanasingh, Chennai (IN); Daniel Sieber, Innsbruck (AT); Andreas Harnisch, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 148 days.

(21) Appl. No.: 15/210,234

(22) Filed: Jul. 14, 2016

(65) Prior Publication Data

US 2017/0014621 A1    Jan. 19, 2017

Related U.S. Application Data

(60) Provisional application No. 62/192,607, filed on Jul. 15, 2015.

(51) Int. Cl.
*A61N 1/05* (2006.01)
(52) U.S. Cl.
CPC .................. *A61N 1/0541* (2013.01)
(58) Field of Classification Search
CPC ........................................ A61N 1/541
USPC ............................................. 607/137
See application file for complete search history.

(56) References Cited

U.S. PATENT DOCUMENTS

| 8,109,705 B1* | 2/2012 | Brown .................... F16B 13/04 |
| | | 248/304 |
| 8,718,795 B2 | 5/2014 | Gibson |
| 8,934,985 B2 | 1/2015 | Dhanasingh et al. |
| 9,155,880 B2 | 10/2015 | Dhanasingh et al. |
| 2002/0095063 A1 | 7/2002 | Kroll et al. |
| 2006/0241723 A1 | 10/2006 | Dadd et al. |

(Continued)

OTHER PUBLICATIONS

International Searching Authority, International Search Report—International Application No. PCT/US16/42241, dated Oct. 7, 2016, together with the Written Opinion of the International Searching Authority, 13 pages.

*Primary Examiner* — Carl H Layno
*Assistant Examiner* — Erin M Piateski
(74) *Attorney, Agent, or Firm* — Sunstein Kann Murphy & Timbers LLP

(57) ABSTRACT

A cochlear implant electrode arrangement is described that prevents post-surgical retraction of the electrode array from the cochlea. The arrangement includes an electrode lead that carries cochlear stimulation signals from an implanted signal processor, through an oval shaped posterior tympanotomy opening in the facial recess of a patient, to an electrode array implanted in a cochlea of the patient. A retraction limiter slides over the electrode lead through the posterior tympanotomy with projection arms aligned along the long diameter of the posterior tympanotomy, then is rotated to align the projection arms along the short diameter of the posterior tympanotomy, and secured to the electrode lead so that the projection arms prevent post-surgical retraction of the electrode lead back through the posterior tympanotomy.

14 Claims, 9 Drawing Sheets

(56) References Cited

U.S. PATENT DOCUMENTS

| | | |
|---|---|---|
| 2007/0088335 A1* | 4/2007 | Jolly ............... A61N 1/0541 604/891.1 |
| 2008/0119920 A1 | 5/2008 | Dadd et al. |
| 2008/0234793 A1* | 9/2008 | Gibson ............ A61N 1/0541 607/137 |
| 2010/0305677 A1* | 12/2010 | Schmidt ........... A61N 1/0541 607/137 |
| 2011/0009877 A1 | 1/2011 | Thenuwara et al. |
| 2011/0245891 A1 | 10/2011 | Fritsch et al. |
| 2015/0032124 A1 | 1/2015 | Lenarz et al. |

* cited by examiner

ELECTRODE LEAD THAT AVOIDS ELECTRODE ARRAY MIGRATION FROM THE COCHLEA

This application claims priority from U.S. Provisional Patent Application 62/192,607, filed Jul. 15, 2015, which is incorporated herein by reference in its entirety.

TECHNICAL FIELD

The present invention relates to medical implants, and more specifically to an implantable electrode arrangement for cochlear implant systems.

BACKGROUND ART

A normal ear transmits sounds as shown in FIG. 1 through the outer ear 101 to the tympanic membrane (eardrum) 102, which moves the bones of the middle ear 103, which in turn vibrate the oval window and round window openings of the cochlea 104. The cochlea 104 is a long narrow duct wound spirally about its axis for approximately two and a half turns. The cochlea 104 includes an upper channel known as the scala vestibuli and a lower channel known as the scala tympani, which are connected by the cochlear duct. The scala tympani forms an upright spiraling cone with a center called the modiolar where the spiral ganglion cells of the acoustic nerve 113 reside. In response to received sounds transmitted by the middle ear 103, the fluid filled cochlea 104 functions as a transducer to generate electric pulses that are transmitted to the cochlear nerve 113, and ultimately to the brain. Hearing is impaired when there are problems in the ability to transduce external sounds into meaningful action potentials along the neural substrate of the cochlea 104.

In some cases, hearing impairment can be addressed by an auditory prosthesis system such as a cochlear implant that electrically stimulates auditory nerve tissue with small currents delivered by multiple stimulation contacts distributed along an implant electrode. FIG. 1 shows some components of a typical cochlear implant system where an external microphone provides an audio signal input to an external signal processing stage 111 which implements one of various known signal processing schemes. The processed signal is converted by the external signal processing stage 111 into a digital data format, such as a sequence of data frames, for transmission into a receiver processor in an implant housing 108. Besides extracting the audio information, the receiver processor in the implant housing 108 may perform additional signal processing such as error correction, pulse formation, etc., and produces a stimulation pattern (based on the extracted audio information) that is sent through an electrode lead 109 to an implanted electrode array 110 which penetrates into the cochlea 104 through a surgical opening in the outer surface of the cochlea 104. Typically, this electrode array 110 includes multiple stimulation contacts 112 on its surface that deliver the stimulation signals to adjacent neural tissue of the cochlea 104 which the brain of the patient interprets as sound. The individual stimulation contacts 112 may be activated sequentially, or simultaneously in one or more contact groups.

To implant the electrode array 110 into the cochlea 104, a posterior tympanotomy is performed at the facial recess opening in the mastoid process of the temporal bone. This involves creating an opening through the mastoid air cells to obtain surgical access from the implant housing 108 which is affixed on the outer surface of the temporal bone beneath the skin behind the pinna of the outer ear 101, to the air space of the middle ear 103. FIG. 2 is a photograph of a facial recess 200 showing the oval shape of the posterior tympanotomy opening that is created, which has a long diameter 201 and a short diameter 202. The electrode array 110 can then be routed from the implant housing 108 through an opening in the outer surface of the cochlea 104.

FIG. 3A shows structural details of a cochlear implant electrode arrangement at the electrode opening 301 into the implanted cochlea 104. After the insertion procedure, the electrode array 110 tends to lie toward the outer lateral wall of the spiral-shaped cochlea 104. Over time, there can be a tendency for the electrode array to spring back and retract back out through the electrode opening 301, as shown in FIG. 3B. The degree of electrode spring back varies depending on how deeply the electrode array 110 is inserted into the cochlea 104, how well the electrode opening 301 is packed with fascia material, and the specific geometry at the electrode opening 301.

Such post-surgical electrode retraction pulls the nearest stimulation contact 112 away from its intended target neural tissue within the cochlea 104 back toward the electrode opening 301, or even further, back outside the cochlea 104 into the middle ear 103. This can produce pain sensation in the patient when that stimulation contact 112 is energized. Usually in such circumstances, that stimulation contact 112 will be inactivated and fewer stimulation contacts 112 remain for use to produce sound sensation. In some cases, an additional revision surgery may even be needed to push the electrode array 110 back inside the cochlea 104.

Various approaches have been attempted to resist such post-surgical retraction by implementing various anti-retraction structures at the electrode opening in the outer surface of the cochlea. A cork-shaped stopper has been used to tightly wedge the electrode lead in the electrode opening. An anti-retraction skirt has been implemented on the electrode array at the electrode opening which is made of polymer material that swells when contacted by the liquid preilymph medium, thereby holding the electrode array in place. Some electrode arrays have a permanent pre-curved shape that does not relax or spring back after insertion into the cochlea. Other electrode arrangements contain an internal malleable material on either side of the electrode opening which maintains a bent shape after full insertion of the electrode array to resist retraction. A surgical group in Hannover Germany has added to the implant electrode a wing of flexible silicone material that can be fixed to a groove in the bony material on the outer surface of the cochlea near the electrode opening. All of these efforts have suffered from various issues that leave each an imperfect solution.

SUMMARY

Embodiments of the present invention are directed to a cochlear implant electrode arrangement that prevents post-surgical retraction. An electrode lead carries cochlear stimulation signals from an implanted signal processor, through an oval shaped posterior tympanotomy opening in the facial recess of a patient, to an electrode array implanted in a cochlea of the patient. A retraction limiter has opposing projection arms, wherein a projection length is defined between the distal ends of the projection arms that is less than the long diameter of the posterior tympanotomy, and greater than the short diameter of the posterior tympanotomy. The retraction limiter is configured to allow sliding the retraction limiter over the electrode lead through the posterior tympanotomy with the projection arms aligned along the long diameter of the posterior tympanotomy, rotating the retraction limiter to align the projection arms along the short diameter of the posterior tympanotomy, and securing the retraction limiter to the electrode lead so that the projection arms prevent post-surgical retraction of the electrode lead back through the posterior tympanotomy.

The retraction limiter may be in the specific form of a slidable clip that has a clip opening configured to allow the retraction limiter to be fit over an outer surface of the electrode lead. There may then be a pair of handling legs that project out at opposing sides of the clip opening to promote surgical handling of the retraction limiter. Or the retraction limiter may be in the specific form of a slidable cylinder that fits over an outer surface of the electrode lead, with a distal cylinder end at which the projection arms are located, and a proximal cylinder end configured to remain outside the posterior tympanotomy after rotating the retraction limiter, wherein the proximal cylinder end of the retraction limiter is configured to be surgically deformed against the electrode lead to secure the retraction limiter to the electrode lead. The retraction limiter may be made of metal or biocompatible plastic material.

Embodiments of the present invention also include a cochlear implant system having an electrode arrangement according to any of the foregoing.

DETAILED DESCRIPTION

Embodiments of the present invention are directed to a cochlear implant electrode arrangement with a retraction limiter at the posterior tympanotomy that resists post-surgical retraction of the inserted electrode lead.

Figure 1:
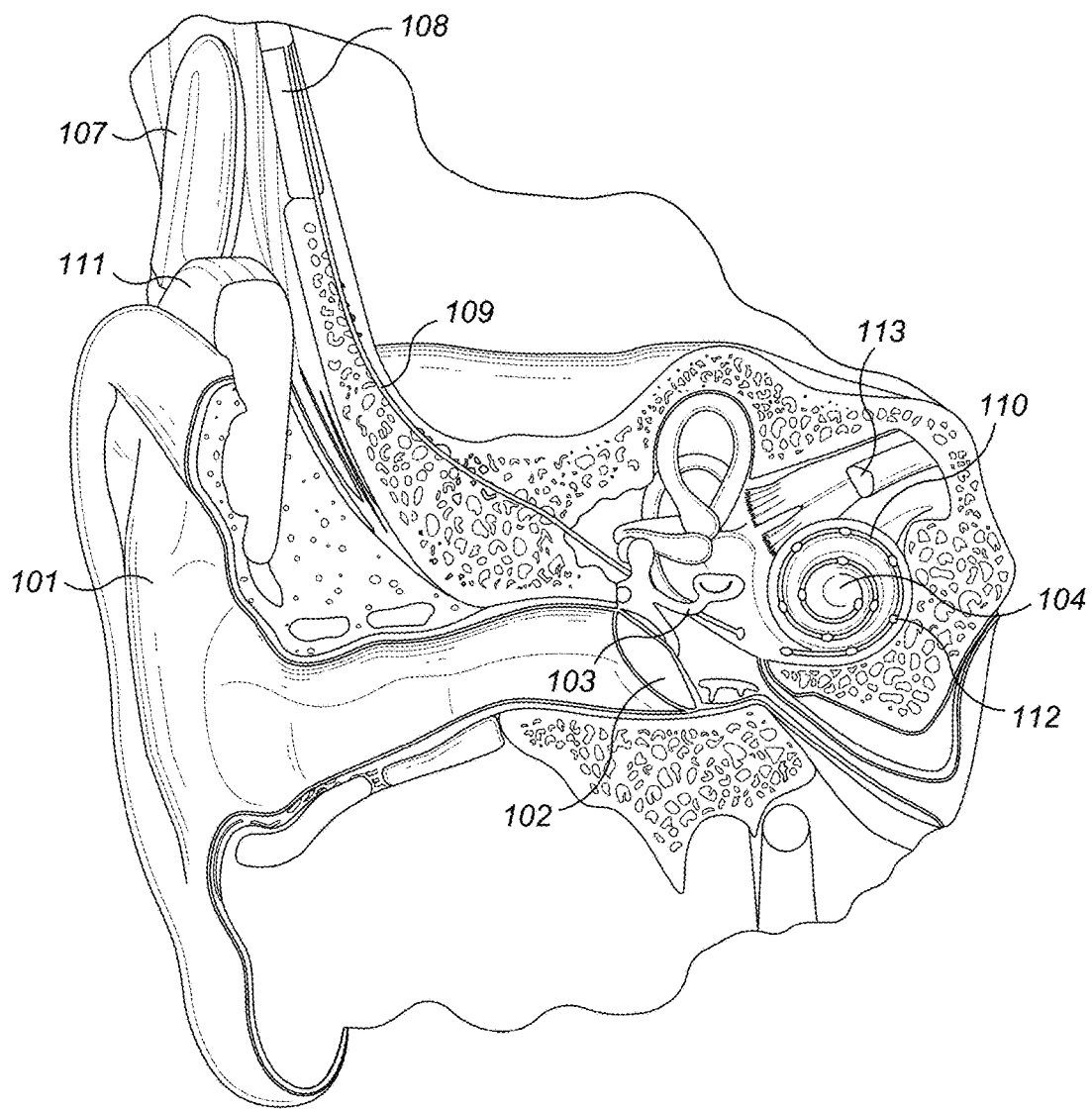
FIG. 1 shows various anatomical structures in a human ear and some components of a typical cochlear implant system.
Figure 2:
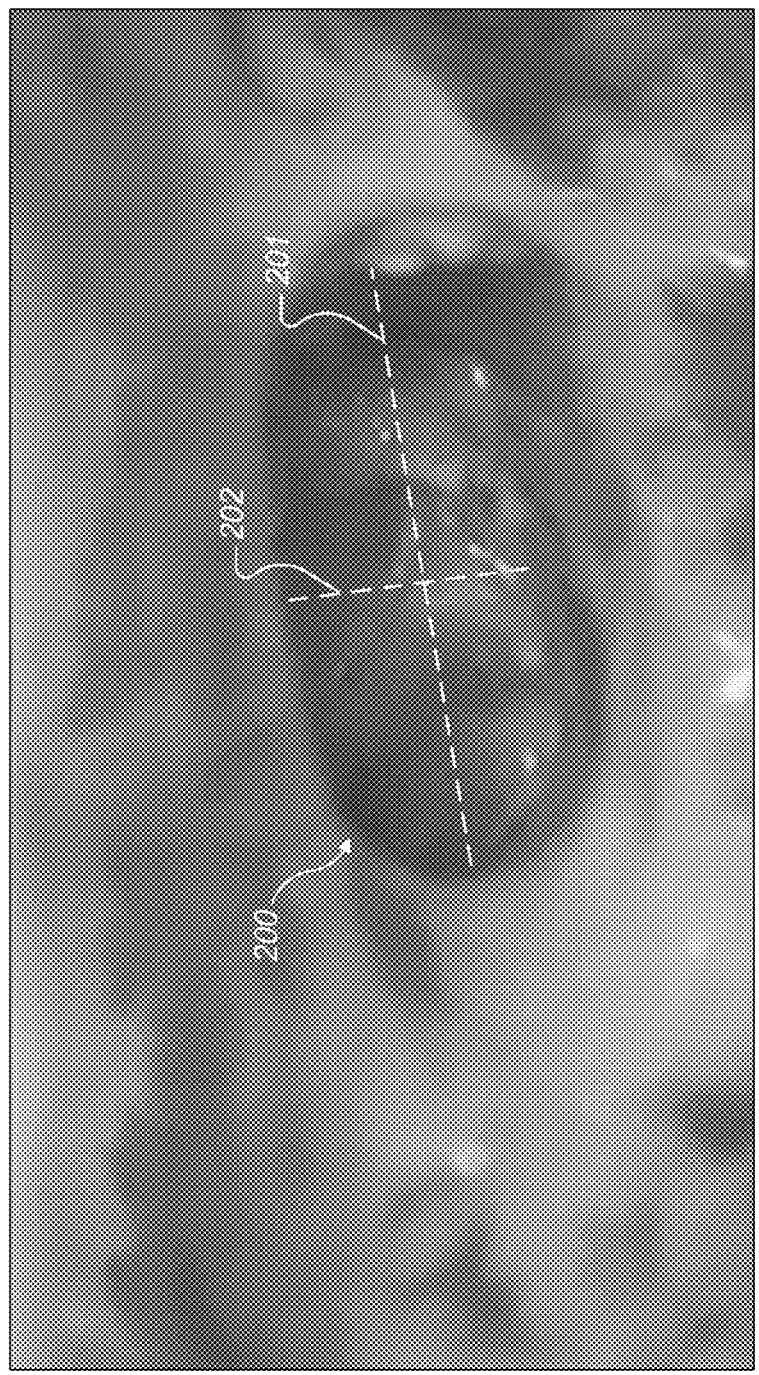
FIG. 2 is a photograph of a typical facial recess with posterior tympanotomy opening.
Figure 3A:
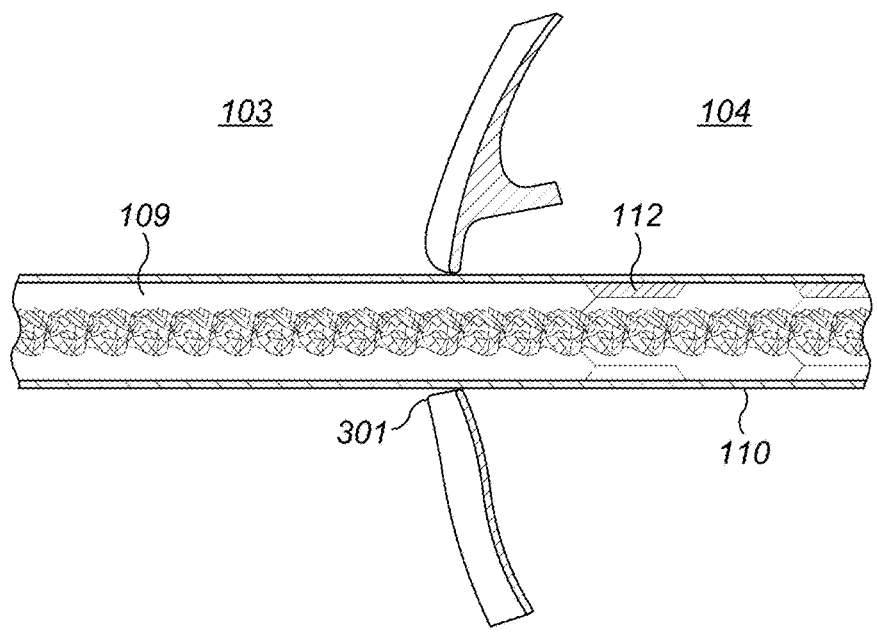
FIG. 3A shows structural details of a cochlear implant electrode arrangement at the electrode opening into the implanted cochlea.
Figure 3B:
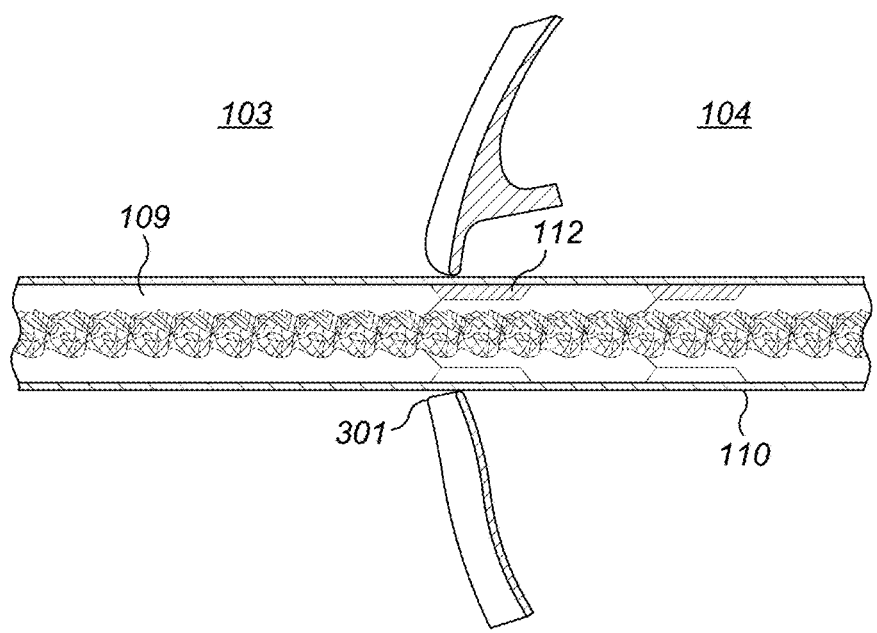
FIG. 3B shows how the proximal end of the intracochlear electrode array can retract back out of the electrode opening to pull the nearest stimulation contact back into the electrode opening.
Figure 4A:
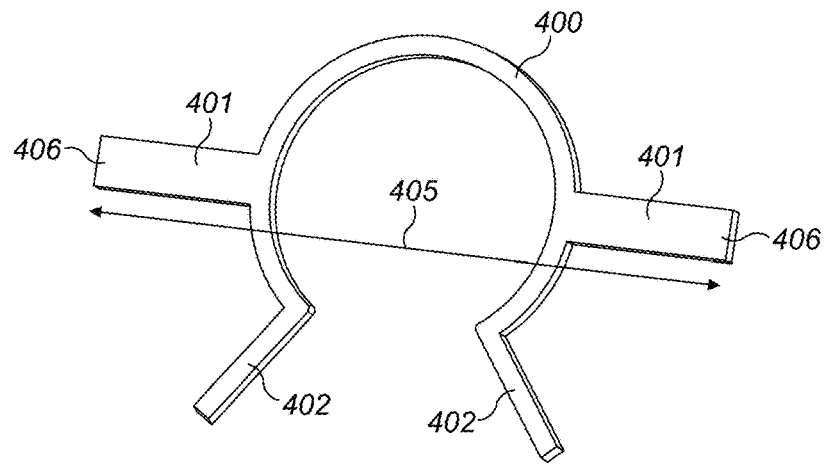
FIG. 4A-4C shows an embodiment of a cochlear implant electrode arrangement having a retraction limiter clip.
Figure 4B:
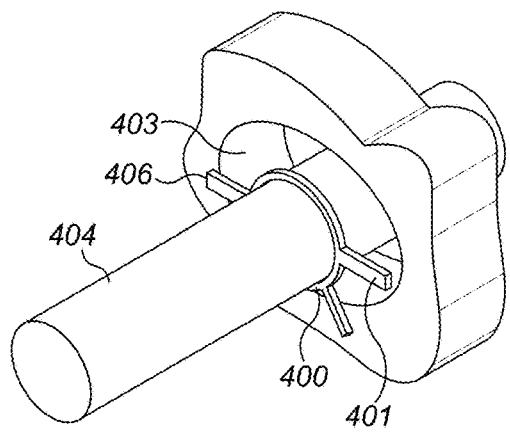
Figure 4C:
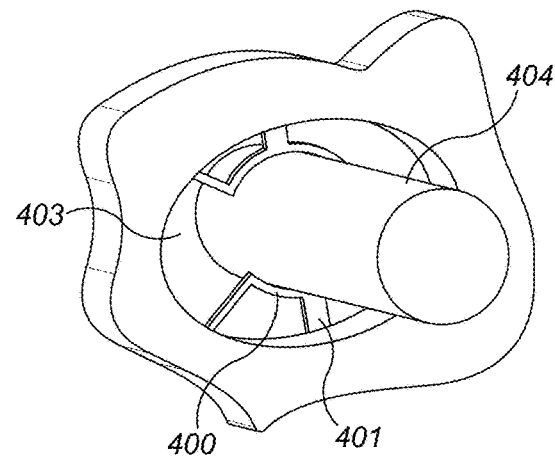

FIG. 4A-4C shows structural details of a portion of a retraction limiter 400 according to one specific embodiment of the present invention. Like most conventional cochlear implant electrode arrangements, there is an electrode lead 404 that carries cochlear stimulation signals from the implanted signal processor (the implant housing) through an oval shaped posterior tympanotomy opening in the facial recess of a patient, to an electrode array 110 that is implanted in a cochlea 104 of the patient. The electrode lead 404 is made of a resilient carrier material as is known in the art and contains electrode wires for carrying the cochlear stimulation signals.

The retraction limiter 400 has opposing projection arms 401 with distal ends 406 that define a projection length 405. The projection length 405 between the distal ends 406 of the projection arms 401 is configured to be less than the long diameter 201 of the posterior tympanotomy 403, and greater than the short diameter 202 of the posterior tympanotomy 403. The retraction limiter 400 also is configured to allow sliding it over the electrode lead 404 through the posterior tympanotomy 403 with the projection arms 401 aligned along the long diameter 201 of the posterior tympanotomy 403, as shown in FIG. 4B. That allows the surgeon to use the handling legs 402 to slide the retraction limiter 400 through the posterior tympanotomy 403, and then rotate it to align the projection arms 401 along the short diameter 202 of the posterior tympanotomy 403, as shown in FIG. 4C. The surgeon can then tightly attach the retraction limiter 400 to the electrode lead 404 so that the projection arms 401 prevent post-surgical retraction of the electrode lead 404 back through the posterior tympanotomy 403; for example, by squeezing together the handling legs 402 and securing them to each other.

Figure 5:
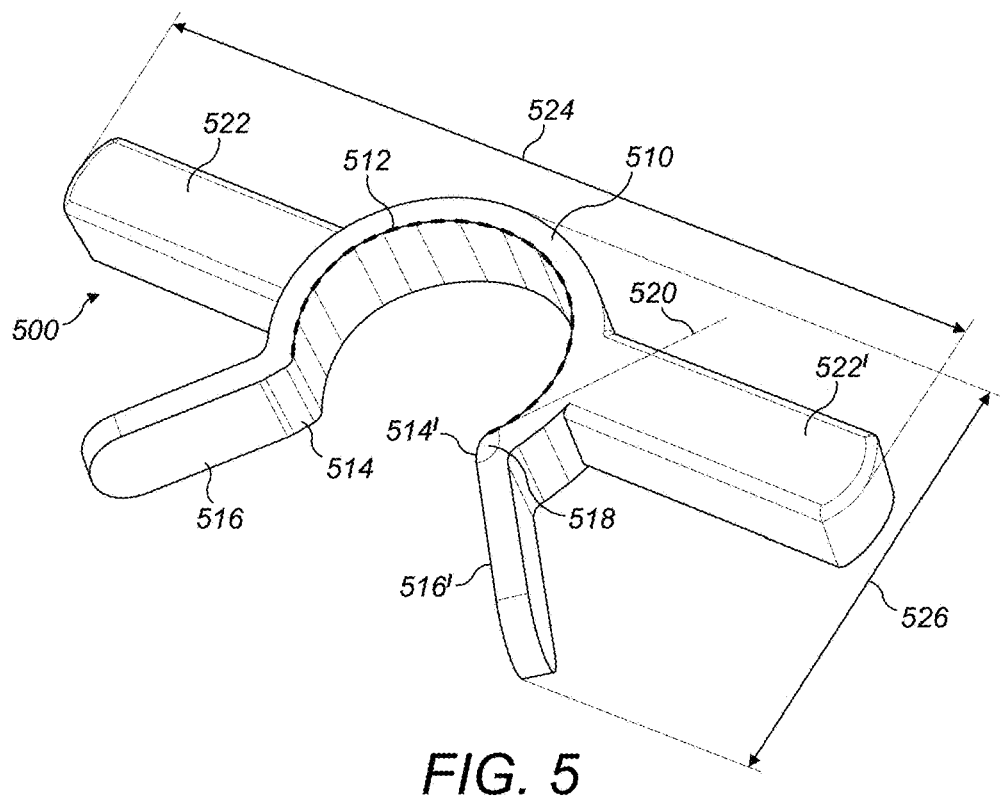
FIG. 5 shows structural details of a retraction limiter clip as in FIG. 4.

FIG. 5 shows structural details of a retraction limiter clip 500 as in FIG. 4, which may be made of metal or a biocompatible plastic material. A central opening 510 matches the shape of the outer surface of the electrode lead 404 which may be inserted through it. For example, if the electrode lead 404 has a cylindrical shape, the central opening 510 of the retainer clip 500 may be circular with a radius that typically would be slightly shorter than the radius of the electrode lead 404 (e.g., about 1.1 mm) to provide useful clamping force. Thus, the inner perimeter 512 of the central opening 510 should be equal to or up to 20% smaller than the outer perimeter of the cylindrical electrode lead 404. The central opening 510 has open ends 514 and 514' at its bottom side, at which there are handling legs 516 and 516' that extend at an angle 518 to the tangent 520 of the curvature of the central opening 510 in this point. These handling legs 516 and 516' serve as a gripping point for the surgeon to secure the retainer clip 500 onto the electrode carrier 404. A second pair of projection arms 522 and 522' extend straight from the central opening 510. The dimensions of the retainer clip 500 are chosen such that the projection length 524 of the projection arms 522 and 522' is slightly less than the long diameter 201 of the oval opening of the posterior tympanotomy, yet longer than the short diameter 202; e.g., between 1 and 2 mm. The clip height 526 is smaller than the short diameter 202. Since the exact dimensions of the posterior tympanotomy 403 will be unknown prior to drilling, a kit may be provided with various retainer clips 500 with different length projection arms 522 and 522'.

Figure 6:
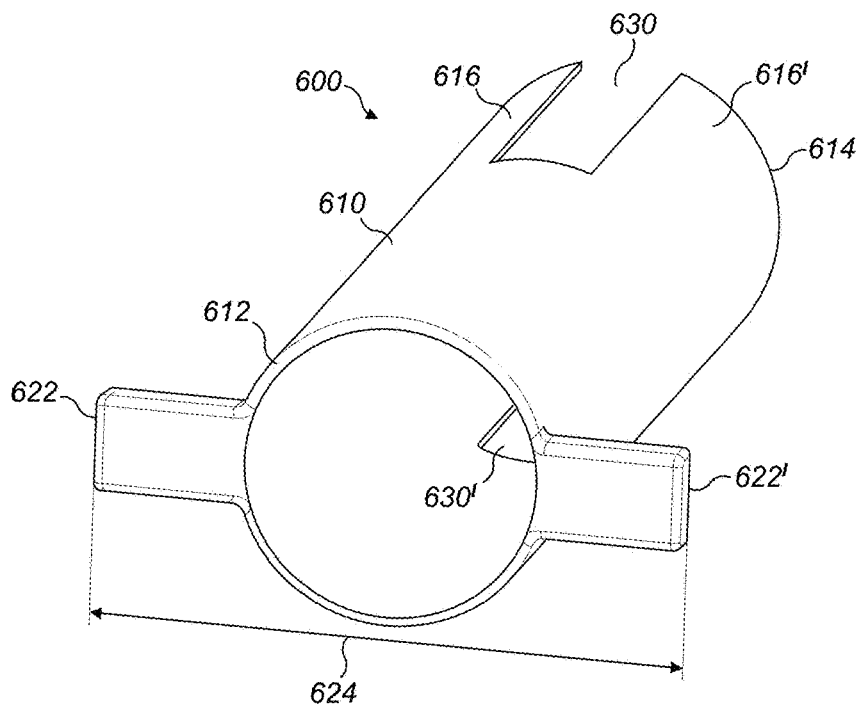
FIG. 6 shows structural details of a retraction limiter cylinder embodiment of the present invention.
Figure 7A:
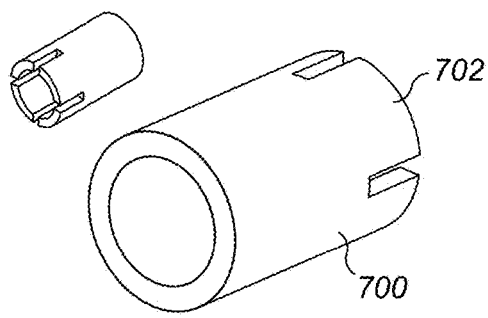
FIG. 7A-7D shows various aspects of another embodiment of a retraction limiter cylinder.
Figure 7B:
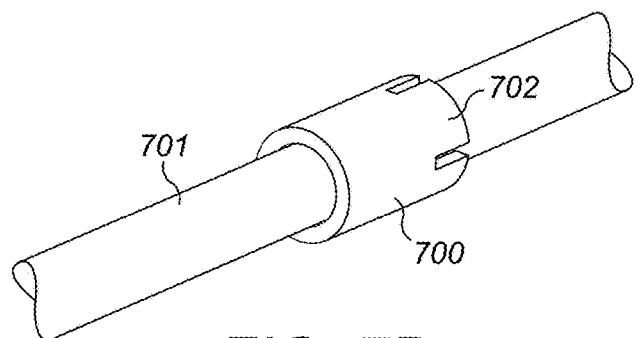
Figure 7C:
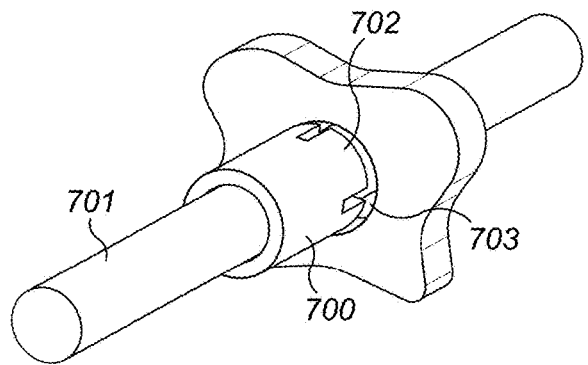
Figure 7D:
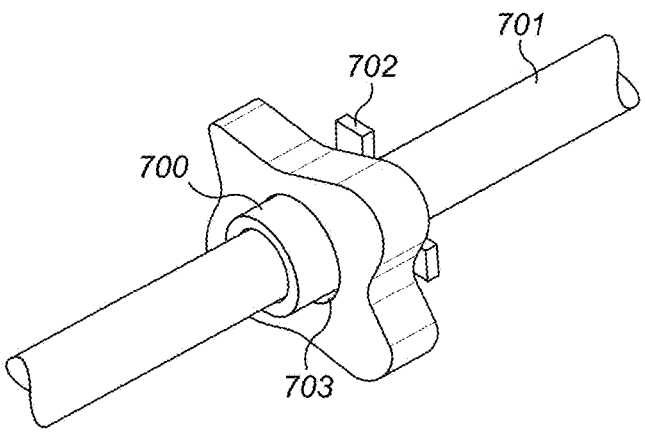

Rather than a clip structure as described above, the retraction limiter may be in the specific form of a cylinder that slides over an outer surface of the electrode lead 404 as shown in FIG. 6. The cylindrical retraction limiter 600 has a cylindrical body 610 with a distal cylinder end 612 at which the projection arms 622 and 622' are located. The proximal end 614 has two end walls 616 and 616' separated by gaps 630 and 630' which are configured to remain outside the posterior tympanotomy after inserting and rotating the retraction limiter 600. The end walls 616 and 616' are then squeezed against the electrode lead 403 to secure the retraction limiter 600 to the electrode lead 404. This arrangement facilitates handling by the surgeon in that the end walls 616 and 616' to be pressed against the electrode lead 404 are, from the surgeon's point of view, on the near side of the posterior tympanotomy 403. The projection arms 622 and 622' define a projection length 624.

FIG. 7A-7D shows various aspects of another embodiment of a cylindrical retraction limiter 700 with four projection fingers 702 circumferentially distributed at the far distal end. Once the electrode array 110 is fully inserted into the cochlea 104, the retraction limiter 700 can be slid down the electrode lead 701 with the projection fingers 702 facing towards the posterior tympanotomy 703, FIG. 7C. Once the projection fingers 702 are pushed through the posterior tympanotomy 703, they are bent about 90° (FIG. 7D) to form an obstruction that blocks the posterior tympanotomy 703. For bending the fingers the surgeon has to push the projection fingers 702 from the outside of the posterior tympanotomy 703. For the oval shape of a typical posterior tympanotomy 703, the surgeon may first bend two opposite projection fingers aligned along the long diameter of the posterior tympanotomy 703, then rotate the retraction limiter 700 by 90° and then bend the other two projection fingers 702. After bending the projection fingers 702, the retraction limiter 700 may be squeezed to deform it so that it holds on the electrode lead 701 tightly.

Figure 8:
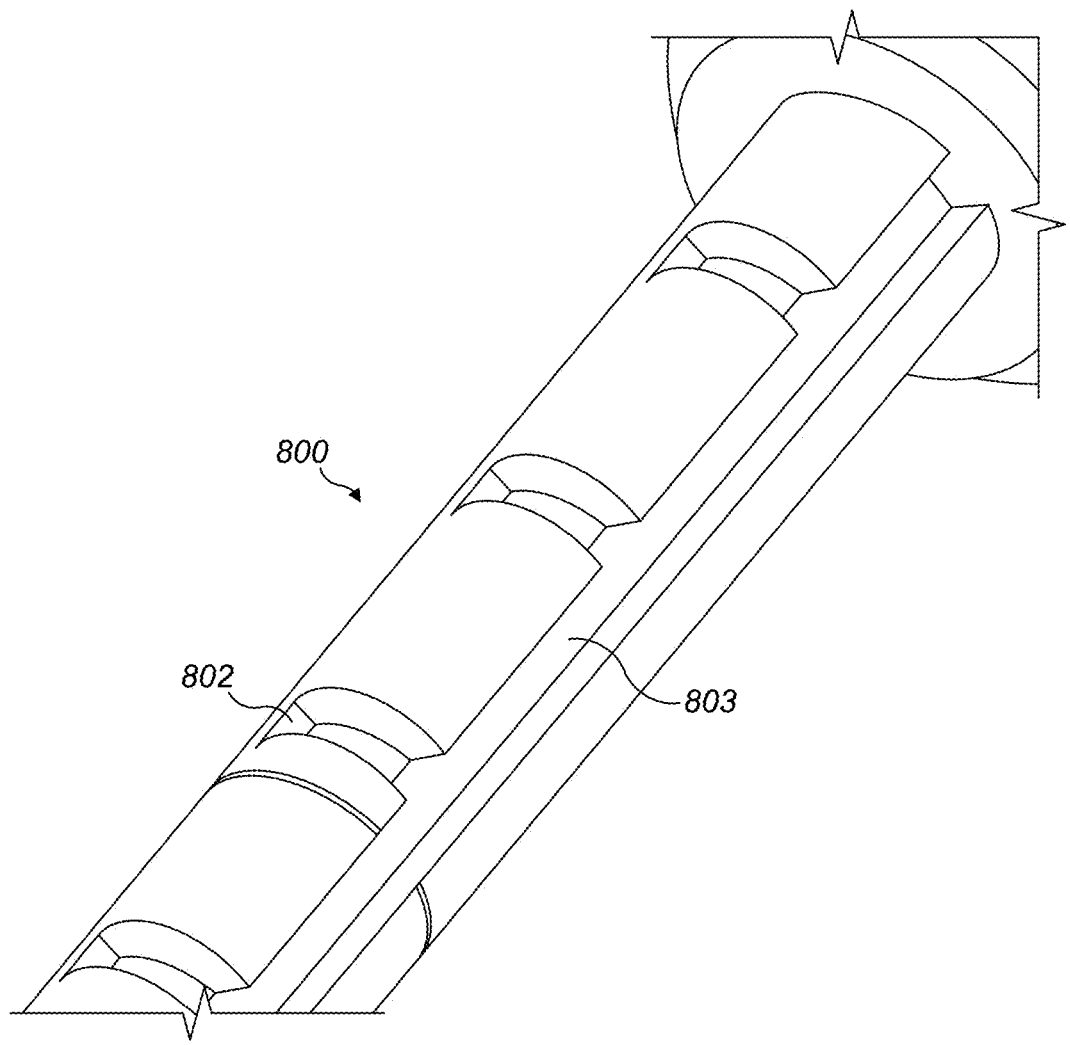
FIG. 8 shows surface details of a cochlear implant electrode lead adapted for use with a retraction limiter according to embodiments of the present invention.

FIG. 8 shows surface details of a cochlear implant electrode lead 800 that is adapted with surface features for use with a retraction limiter according to various of the embodiments of the present invention. In the specific embodiment shown in FIG. 8, the electrode lead 800 has multiple locking grooves 802 on its outer surface that are perpendicular to the longitudinal axis of the electrode lead 800 and offer a purchase for the retraction limiter to secure it in place. Also shown in the electrode 800 in FIG. 8 is a longitudinal sliding groove 803 that acts as a sliding rail to guide the retraction limiter along the outer surface of the electrode lead 800.

Figure 9A:
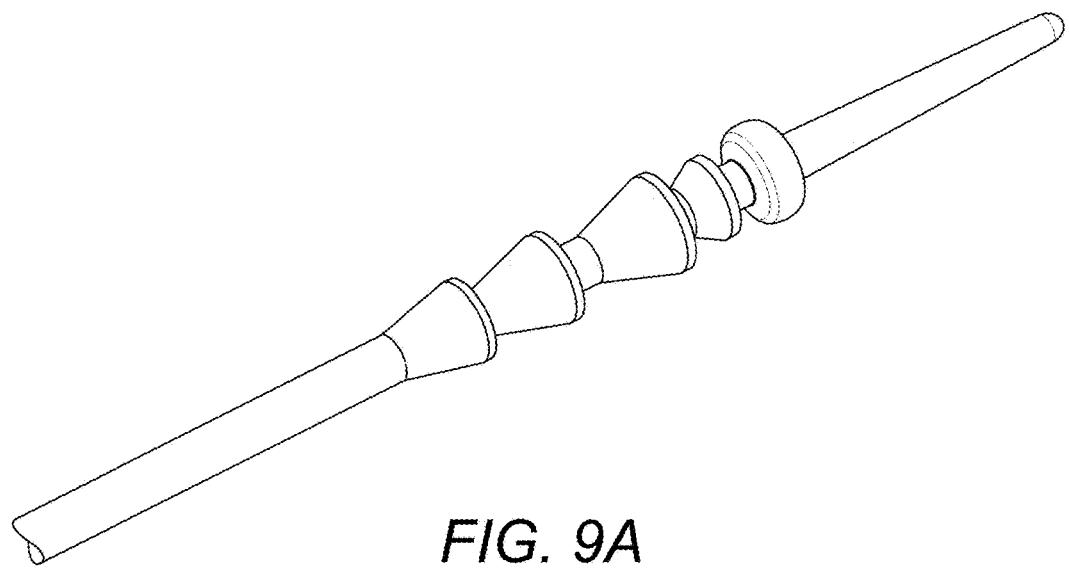
FIG. 9A-9D shows structural details of a cochlear implant electrode lead adapted for use with a retraction limiter according to embodiments of the present invention.
Figure 9B:
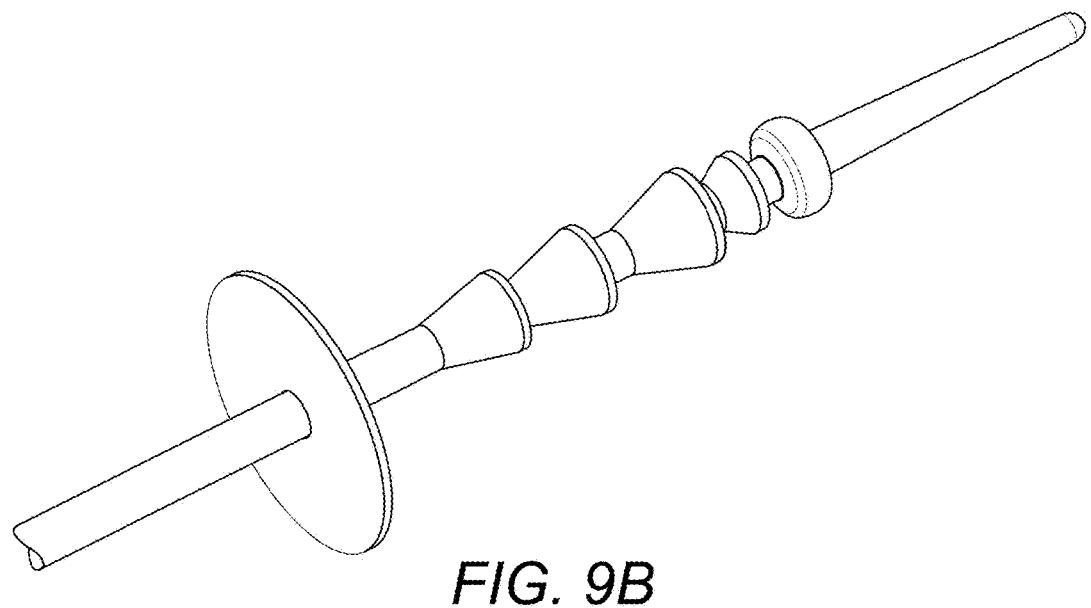
Figure 9C:
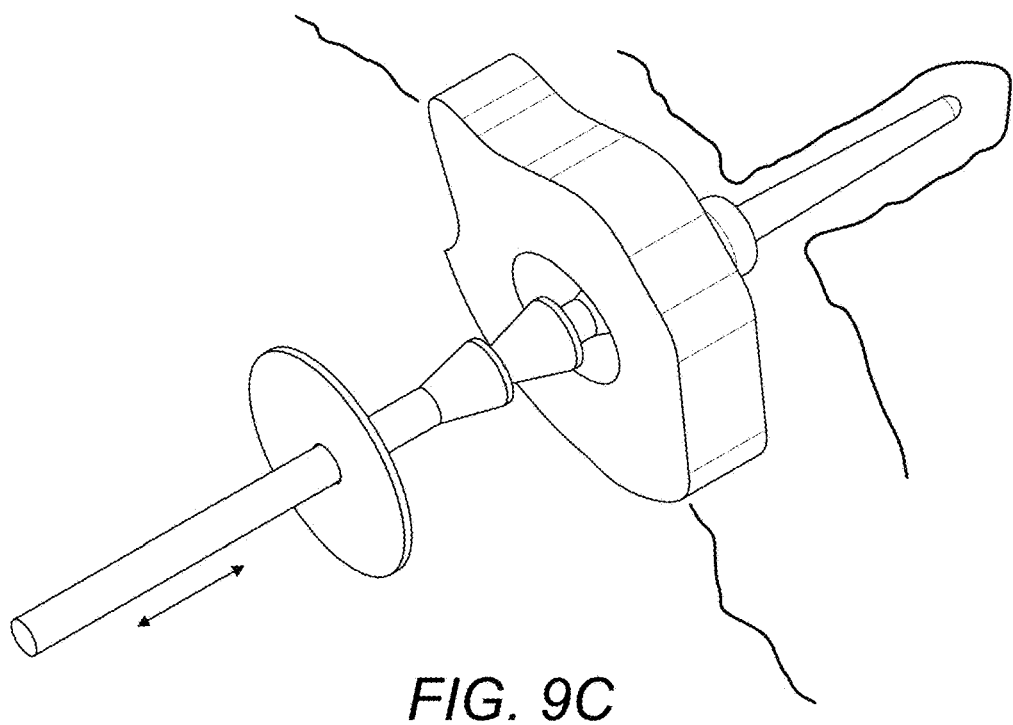
Figure 9D:
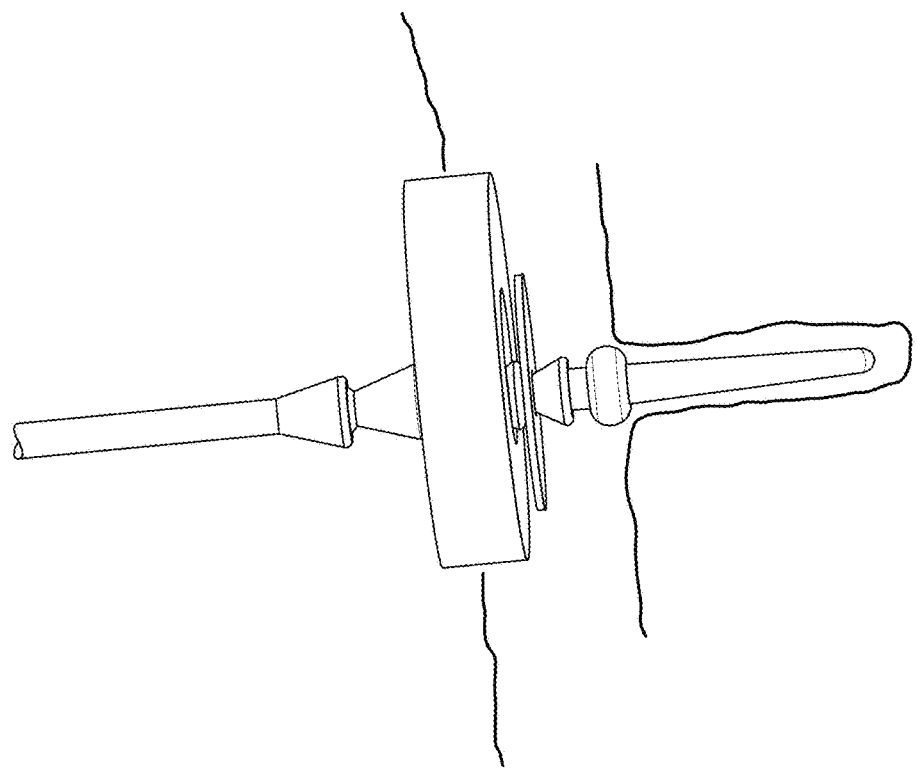

FIG. 9A-9D shows structural details of a cochlear implant electrode lead with inverted cork shaped projection features according to embodiments of the present invention. Conventional cork structures for the purpose of an implant fixation are also shown in U.S. Pat. No. 4,892,108 and European Patent 1972359, but embodiments of the present invention use an inverted cork orientation. The electrode lead can have inverted cork like features along the lead length as shown in FIG. 9A, and/or a flexible extended ring as shown in FIG. 9B. After the electrode array is fully inserted into the cochlea, the flexible extended ring can be moved to the inside of the posterior tympanotomy and the flexible extended ring becomes wedged between the skull bone and the closest inverted cork as shown in FIGS. 9C and 9D, thereby preventing the electrode from springing back.

Although various exemplary embodiments of the invention have been disclosed, it should be apparent to those skilled in the art that various changes and modifications can be made which will achieve some of the advantages of the invention without departing from the true scope of the invention.

What is claimed is:

1. A cochlear implant electrode arrangement comprising:
an electrode lead configured to carry cochlear stimulation signals from a signal processor through an oval shaped posterior tympanotomy in a facial recess of a patient;
an electrode array having stimulation contacts on a surface of the electrode array, the stimulation contacts configured to deliver the stimulation signals from the electrode lead to adjacent neural tissue of a cochlea of the patient; and
a retraction limiter having a central opening that surrounds at least a portion of an outer surface of the electrode lead, the retraction limiter having a projection length and a height and having opposing projection arms and a pair of securing ends, the securing ends configured to be moved closer to one another in order to make the central opening smaller, each projection arm having a distal end, wherein the projection length is defined between the distal ends of the projection arms and the height is less than the projection length, and the projection length is configured to be
less than a long diameter of the posterior tympanotomy and
greater than a short diameter of the posterior tympanotomy, and the height is configured to be less than the short diameter of the posterior tympanotomy,
wherein the retraction limiter is configured:
i. to slide over the electrode lead to a proximal end of the electrode array with the projection arms at a first position,
ii. to rotate relative to the electrode lead in order to align the projection arms in a second position approximately 90 degrees from the first position, and
iii. to be secured to the electrode lead when the securing ends are moved closer to one another in order to prevent further movement of the retraction limiter relative to the electrode lead.

2. The electrode arrangement according to claim 1, wherein the central opening partially surrounds the electrode lead so that the retraction limiter forms a slidable clip having a clip opening with two open ends at a bottom of the central opening, the clip opening configured to allow the electrode lead to fit between the two open ends when the retraction limiter is placed around the outer surface of the electrode lead.

3. The electrode arrangement according to claim 2, wherein one of the securing ends projects out at an angle from each of the open ends of the clip opening.

4. The electrode arrangement according to claim 1, wherein the central opening fully surrounds the electrode lead so that the retraction limiter forms a slidable cylinder that fits over the outer surface of the electrode lead, the retraction limiter having:
i. a distal cylinder end at which the projection arms are located, the distal cylinder end adjacent to the proximal end of the electrode array, and
ii. a proximal cylinder end that includes the securing ends separated by gaps that extend along a longitudinal direction of the cylinder,
wherein the securing ends are configured to be deformed against the electrode lead to secure the retraction limiter to the electrode lead.

5. The electrode arrangement of claim 1, wherein the retraction limiter is made of metal material.

6. The electrode arrangement of claim 1, wherein the retraction limiter is made of biocompatible plastic material.

7. The electrode arrangement of claim 3, wherein the securing ends are configured to be moved closer to one another by squeezing the securing ends together, and further configured to be secured to one another.

8. A cochlear implant system comprising a cochlear implant electrode arrangement according to claim 1.

9. The cochlear implant system according to claim 8, wherein the central opening partially surrounds the electrode lead so that the retraction limiter forms a slidable clip having a clip opening with two open ends at a bottom of the central opening, the clip opening configured to allow the electrode lead to fit between the two open ends when the retraction limiter is placed around the outer surface of the electrode lead.

10. The cochlear implant system according to claim 9, wherein one of the securing ends projects out at an angle from each of the open ends of the clip opening.

11. The cochlear implant system according to claim 10, wherein the securing ends are configured to be moved closer to one another by squeezing the securing ends together, and further configured to be secured to one another.

12. The cochlear implant system according to claim 8, wherein the central opening fully surrounds the electrode lead so that the retraction limiter forms a slidable cylinder that fits over the outer surface of the electrode lead, the retraction limiter having:
   i. a distal cylinder end at which the projection arms are located, the distal cylinder end adjacent to the proximal end of the electrode array, and
   ii. a proximal cylinder end that includes the securing ends separated by gaps that extend along a longitudinal direction of the cylinder, wherein the securing ends are configured to be deformed against the electrode lead to secure the retraction limiter to the electrode lead.

13. The cochlear implant system according to claim 8, wherein the retraction limiter is made of metal material.

14. The cochlear implant system according to claim 8, wherein the retraction limiter is made of biocompatible plastic material.

* * * * *